US008821401B2

United States Patent
Baba et al.

(10) Patent No.: US 8,821,401 B2
(45) Date of Patent: Sep. 2, 2014

(54) ULTRASONIC DIAGNOSTIC APPARATUS, DOPPLER MEASUREMENT APPARATUS, AND DOPPLER MEASUREMENT METHOD

(75) Inventors: Tatsuro Baba, Otawara (JP); Naohisa Kamiyama, Otawara (JP); Shouichi Nakauchi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 12 days.

(21) Appl. No.: 13/150,284

(22) Filed: Jun. 1, 2011

(65) Prior Publication Data
US 2011/0230764 A1 Sep. 22, 2011

Related U.S. Application Data

(63) Continuation of application No. PCT/JP2009/070260, filed on Dec. 2, 2009.

(30) Foreign Application Priority Data

Dec. 2, 2008 (JP) .................................. 2008-307885

(51) Int. Cl.
*A61B 8/00* (2006.01)
*A61B 8/06* (2006.01)
(52) U.S. Cl.
CPC .. *A61B 8/06* (2013.01); *A61B 8/543* (2013.01)
USPC ............................ 600/437; 600/440; 600/441
(58) Field of Classification Search
USPC .......................................... 600/437, 440, 441
See application file for complete search history.

(56) References Cited

U.S. PATENT DOCUMENTS

| 8,128,565 B2* | 3/2012 | Ohtake et al. ............... 600/441 |
| 2006/0084873 A1* | 4/2006 | Baba et al. .................... 600/441 |
| 2008/0114240 A1* | 5/2008 | Sasaki ........................... 600/440 |

FOREIGN PATENT DOCUMENTS

| JP | 8-229039 | 9/1996 |
| JP | 2003-135465 | 5/2003 |
| JP | 2003-284718 | 10/2003 |
| JP | 2008-532658 | 8/2008 |
| WO | WO 2006/096915 A1 | 9/2006 |

OTHER PUBLICATIONS

International Search Report mailed Mar. 2, 2010 in PCT/JP2009/070260 filed Dec. 2, 2009 (English Translation).
International Written Opinion mailed Mar. 2, 2011 in PCT/JP2009/070260 filed Dec. 2, 2009.

* cited by examiner

*Primary Examiner* — Peter Luong
(74) *Attorney, Agent, or Firm* — Oblon, Spivak, McClelland, Maier & Neustadt, L.L.P.

(57) ABSTRACT

According to one embodiment, an ultrasonic diagnostic apparatus comprises a Doppler processing unit which generates a Doppler spectrum from an ultrasonic signal reflected from a predetermined region in a heart, a trace waveform generation unit which generates temporal changes in a predetermined spectrum component in the Doppler spectrum as a plurality of trace waveforms, a corrected trace waveform generation unit which generates a corrected trace waveform with the loss being interpolated by using a trace waveform, of the plurality of trace waveforms, which has a loss portion, and at least one estimation point input for the trace waveform, and an output unit which outputs a plurality of trace waveforms including the corrected trace waveform.

10 Claims, 13 Drawing Sheets

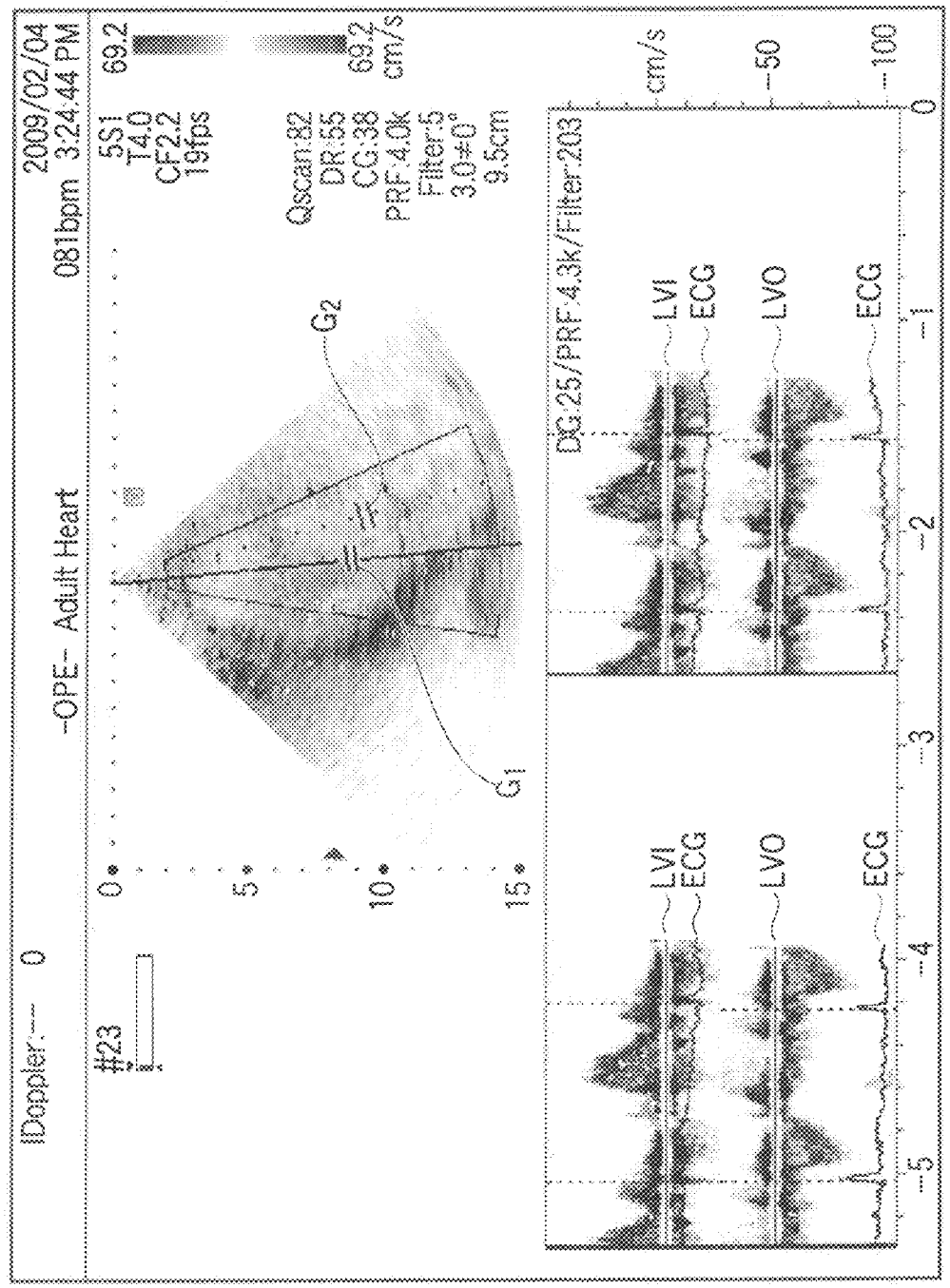
F I G. 13

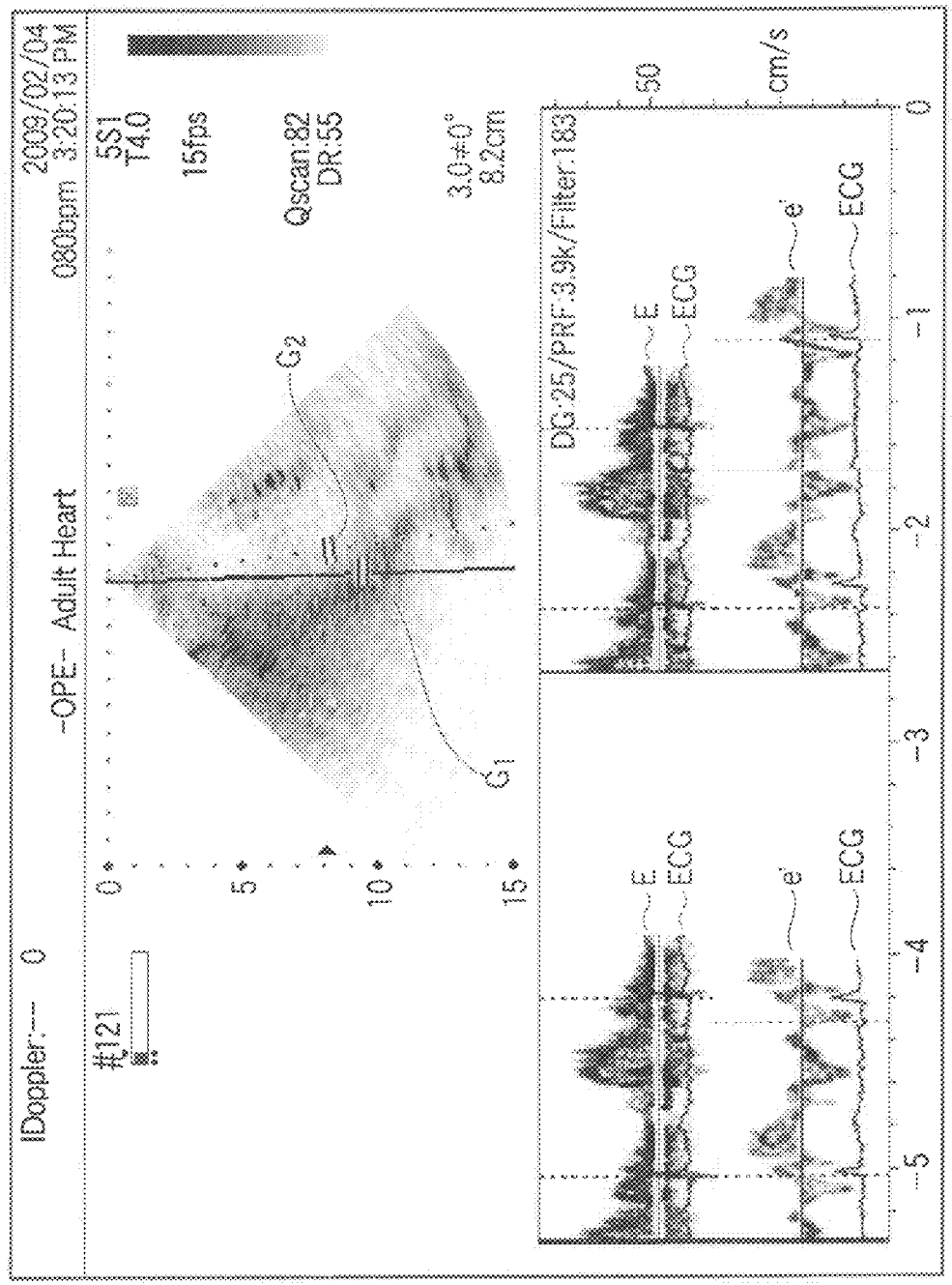
F I G. 15

ULTRASONIC DIAGNOSTIC APPARATUS, DOPPLER MEASUREMENT APPARATUS, AND DOPPLER MEASUREMENT METHOD

CROSS REFERENCE TO RELATED APPLICATIONS

This is a Continuation Application of PCT Application No. PCT/JP2009/070260, filed Dec. 2, 2009, which was published under PCT Article 21(2) in Japanese.

This application is based upon and claims the benefit of priority from Japanese Patent Application No. 2008-307885, filed Dec. 2, 2008; the entire contents of which are incorporated herein by reference.

FIELD

Embodiments described herein relate generally to an ultrasonic diagnostic apparatus, Doppler measurement apparatus, and Doppler measurement method which can execute cardiac Doppler measurement.

BACKGROUND

Ultrasonic diagnosis allows to display in real time how the heart beats or the fetus moves, by simply bringing an ultrasonic probe into contact with the body surface. This technique is highly safe, and hence allows repetitive examination. Furthermore, this system is smaller in size than other diagnostic apparatuses such as X-ray, CT, and MRI apparatuses. This technique can therefore be said to be a simple diagnostic technique which facilitates examination to be performed by moving the apparatus to the bed side. Ultrasonic diagnostic apparatuses used in this ultrasonic diagnosis vary in type depending on the functions which they have. Some compact apparatuses which have already been developed are small enough to be carried with one hand, and ultrasonic diagnosis is free from the influence of radiation exposure unlike diagnosis using X-rays. Therefore, such ultrasonic diagnostic apparatuses can be used in obstetric treatment, treatment at home, and the like.

A Doppler spectrum method is available as a method of obtaining blood flow information in a blood vessel or the heart in an object quantitatively with high accuracy in such ultrasonic diagnosis. The Doppler spectrum method ultrasonically scans a desired region in a blood vessel or in the heart, and performs computation such as FFT for a reception signal corresponding to a desired range gate, thereby obtaining a Doppler spectrum (Doppler frequency). This Doppler spectrum is a graph (waveform) with the abscissa representing the time, and the ordinate representing the frequency, and expresses the intensity of each frequency component as the luminance of an image. In addition, in order to evaluate the function of a cardiac such as the heart, various kinds of measurement values such as left ventricular inflow and outflow are calculated from the obtained Doppler spectrum.

In general, however, cardiac Doppler measurement (in particular, in the cardiac cavity) may not be able to acquire a proper Doppler spectrum due to the mixing of unnecessary signals from a valve or a tendinous chord owing to arrhythmia or the like. In such a case, the operator manually corrects an imperfect Doppler spectrum, manually calculates measurement values from a selected Doppler spectrum, or redoes measurement. In addition, only limited parameters have been automatically calculated in Doppler measurement, and hence the operator has manually calculated several parameters associated with a blood flow. This complicates operation in cardiac Doppler measurement, resulting in a factor that reduces diagnostic efficiency.

In consideration of the above situation, it is provided that an ultrasonic diagnostic apparatus, Doppler measurement apparatus, and Doppler measurement method which can automate or semi-automate various kinds of manual procedures occupying most of the operation in cardiac Doppler measurement, and attribute to a reduction in operation load in cardiac Doppler measurement, an improvement in operation efficiency, and a reduction in variations in measurement result.

BRIEF DESCRIPTION OF THE DRAWINGS

FIG. 2A is a view showing an example of a Doppler spectrum with a loss or the like.

FIG. 2B is a view showing an example of a Doppler spectrum with a loss or the like.

FIG. 3A is a view showing an example of a trace waveform with losses and the like.

FIG. 3B is a view showing an example of a trace waveform with losses and the like.

FIG. 6 is a view for explaining interpolation processing using the position of a peak velocity Vp and the like.

FIG. 7 is a view for explaining interpolation processing using the position of the peak velocity Vp and the like.

FIG. 13 is a view showing an example of how the first Doppler spectrum measured at the position of a first gate G1 and the second spectrum measured at the position of a second gate G2 are simultaneously displayed in correspondence with cardiac phases.

FIG. 15 is a view for explaining a modification of the third embodiment.

DETAILED DESCRIPTION

Figure 1:
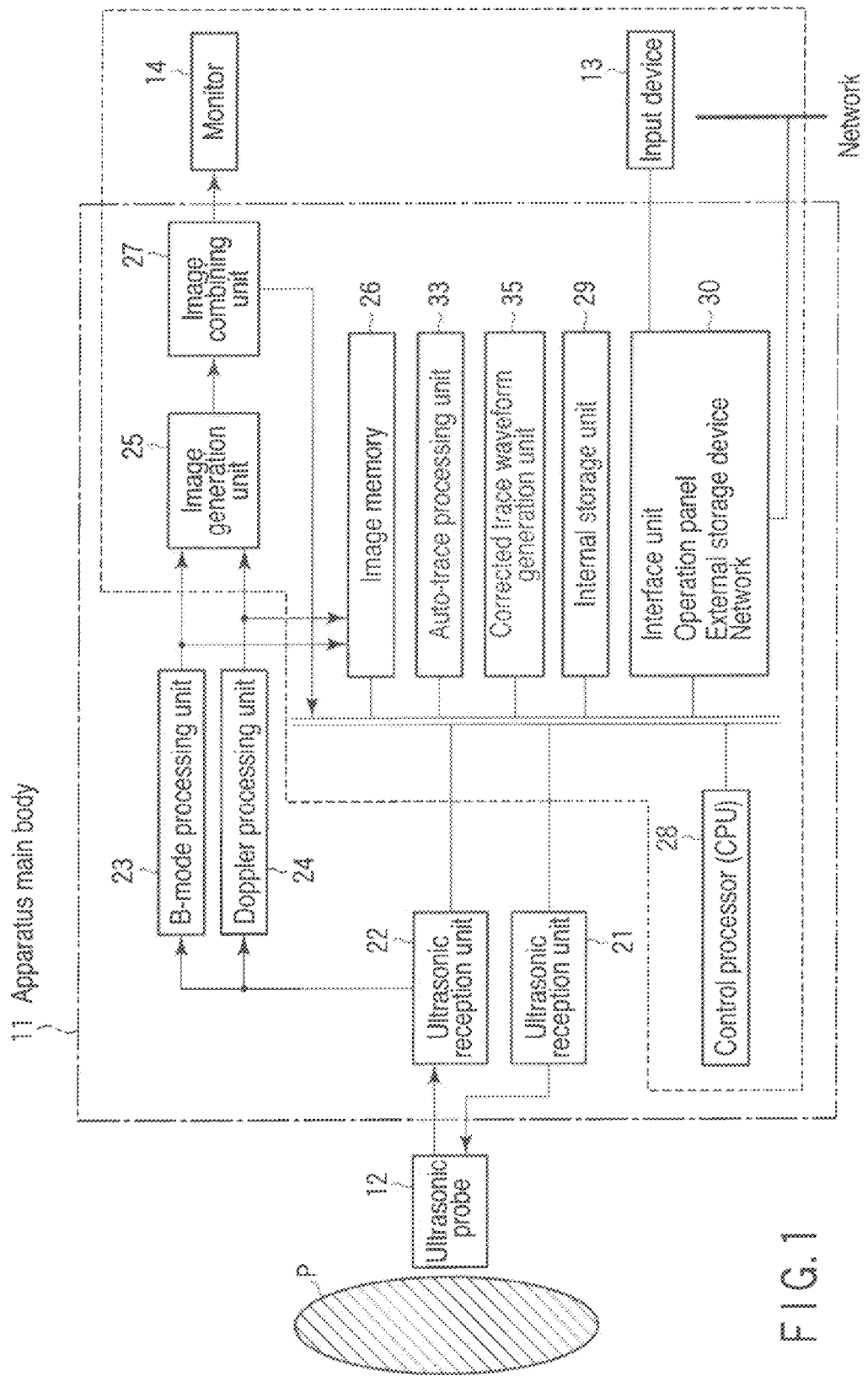
FIG. 1 is a block diagram showing the arrangement of an ultrasonic diagnostic apparatus according to the first embodiment.

In general, according to one embodiment, an ultrasonic diagnostic apparatus comprises a Doppler processing unit which generates a Doppler spectrum from an ultrasonic signal reflected from a predetermined region in a heart, a trace waveform generation unit which generates temporal changes in a predetermined spectrum component in the Doppler spectrum as a plurality of trace waveforms, a corrected trace waveform generation unit which generates a corrected trace waveform with the loss being interpolated by using a trace waveform, of the plurality of trace waveforms, which has a loss portion, and at least one estimation point input for the trace waveform, and an output unit which outputs a plurality of trace waveforms including the corrected trace waveform.

The embodiments will be described below with reference to the views of the accompanying drawing. Note that the same reference numerals in the following description denote constituent elements having almost the same functions and arrangements, and a repetitive description will be made only when required.

FIG. 1 is a block diagram showing the arrangement of an ultrasonic diagnostic apparatus according to the first embodiment. As shown in FIG. 1, an ultrasonic diagnostic apparatus 11 of this embodiment includes an ultrasonic probe 12, an input device 13, a monitor 14, an ultrasonic transmission unit 21, an ultrasonic reception unit 22, a B-mode processing unit 23, a Doppler processing unit 24, an image generation unit 25, an image memory 26, a control processor (CPU) 28, an internal storage unit 29, an interface unit 30, an auto-trace processing unit 33, and a corrected trace waveform generation unit 35. The function of each constituent element will be described below.

The ultrasonic probe 12 includes a plurality of piezoelectric transducers which generate ultrasonic waves based on driving signals from the ultrasonic transmission unit 21 and convert reflected waves from an object into electrical signals, a matching layer provided for the piezoelectric transducers, and a backing member which prevents ultrasonic waves from propagating backward from the piezoelectric transducers. When ultrasonic waves are transmitted from the ultrasonic probe 12 to an object P, the transmitted ultrasonic waves are sequentially reflected by the discontinuity surface of acoustic impedance of an internal body tissue, and are received as echo signals by the ultrasonic probe 12. The amplitude of such an echo signal depends on an acoustic impedance difference on the discontinuity surface by which the echo signal is reflected. The echo produced when a transmitted ultrasonic pulse is reflected by the surface of a moving blood flow, cardiac wall, or the like is subjected to a frequency shift depending on the velocity component of the moving body in the ultrasonic transmission direction due to the Doppler effect.

The input device 13 includes various types of switches, buttons, a trackball, a mouse, and a keyboard which are used to input, to the apparatus main body 11, various types of instructions and conditions, an instruction to set a region of interest (ROI), various types of image quality condition setting instructions, and the like from an operator. When, for example, the operator operates the end button or FREEZE button of the input device 13, the transmission/reception of ultrasonic waves is terminated, and the ultrasonic diagnostic apparatus is set in a pause state.

The monitor 14 displays morphological information (B-mode images) in the living body, blood flow information (a mean velocity image, variance image, power image, and the like), and their combinations as images based on video signals from the scan converter 25.

The ultrasonic transmission unit 21 includes a trigger generation circuit, delay circuit, and pulser circuit (none of which are shown). The pulser circuit repeatedly generates rate pulses for the formation of transmission ultrasonic waves at a predetermined rate frequency fr Hz (period: 1/fr sec). The delay circuit gives each rate pulse the delay time required to focus ultrasonic waves into a beam for each channel and determine a transmission directivity. The trigger generating circuit applies a driving pulse to the probe 12 at the timing based on this rate pulse.

The ultrasonic reception unit 22 includes an amplifier circuit, A/D converter, and adder (none of which are shown). The amplifier circuit amplifies an echo signal received via the probe 12 for each channel. The A/D converter gives the amplified echo signals delay times necessary to determine reception directivities. The adder then performs addition processing for the signals. With this addition, a reflection component from a direction corresponding to the reception directivity of the echo signal is enhanced to form a composite beam for ultrasonic transmission/reception in accordance with reception directivity and transmission directivity.

The B-mode processing unit 23 receives an echo signal from the transmission/reception unit 21, and performs logarithmic amplification, envelope detection processing, and the like for the signal to generate data whose signal intensity is expressed by a luminance level. The scan converter 25 causes the monitor 14 to display, as a B-mode image, this data whose reflected wave intensity is expressed by a luminance.

The Doppler processing unit 24 frequency-analyzes velocity information from the echo signal received from the transmission/reception unit 21 to extract a blood flow, tissue, and contrast medium echo component by the Doppler effect, and obtains blood flow information such as a mean velocity, variance, and power at multiple points.

The image generation unit 26 generates an ultrasonic diagnostic image as a display image by converting (scan-converting) the scanning line signal string for ultrasonic scanning into a scanning line signal string in a general video format typified by a TV format.

The image memory (cine memory) 26 is a memory which stores, for example, ultrasonic images corresponding to a plurality of frames immediately before a freeze. Continuously displaying (cine-displaying) images stored in the image memory 26 can display an ultrasonic moving image.

The control processor 28 has the function of an information processing apparatus (computer) and controls the operation of the main body of this ultrasonic diagnostic apparatus. The control processor 28 reads out, from the internal storage unit 29, a dedicated program for implementing a trace waveform correction function (to be described later), and predetermined control programs for executing image generation/display and the like, expands the programs in its own memory, and executes computation, control, and the like associated with each type of processing.

The internal storage unit 29 stores dedicated programs for implementing a predetermined scan sequence and a trace waveform correction function (to be described later), control programs for executing image generation and display processing, diagnosis information (patient ID, findings by doctors, and the like), a diagnostic protocol, transmission/reception conditions, a body mark generation program, and other data. The internal storage unit 29 is also used to store images in the image memory 26, as needed. It is possible to transfer data in the internal storage unit 29 to an external peripheral device via the interface unit 30.

The interface unit 30 is an interface associated with the input device 13, a network, and a new external storage device (not shown). The interface unit 30 can transfer, via a network, data such as ultrasonic images, analysis results, and the like obtained by this apparatus to another apparatus.

The auto-trace processing unit 33 executes the auto-trace processing of automatically tracing the maximum flow velocity at each time with respect to time-series Doppler spectrum data acquired by Doppler measurement.

The corrected trace waveform generation unit 35 executes trace waveform correction processing (to be described later) under the control of the control processor 28.

(Trace Waveform Correction Function)

Figure 2A:
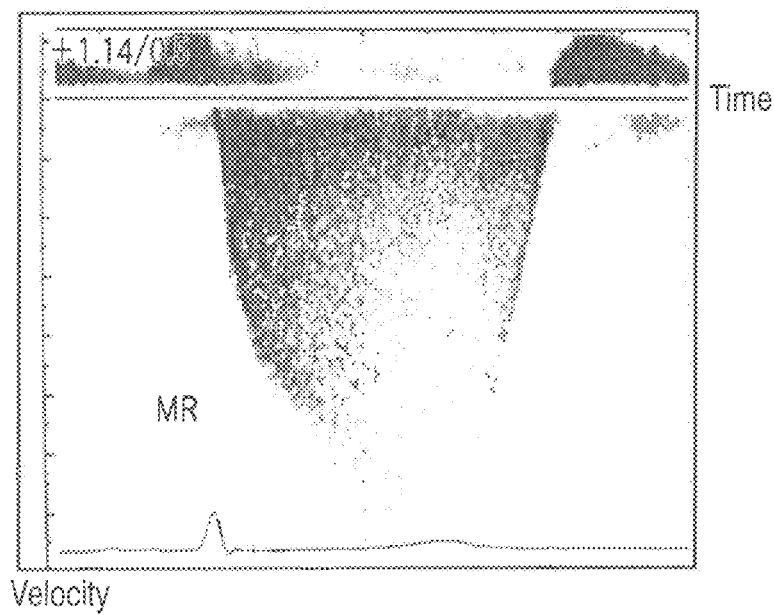
Figure 2B:
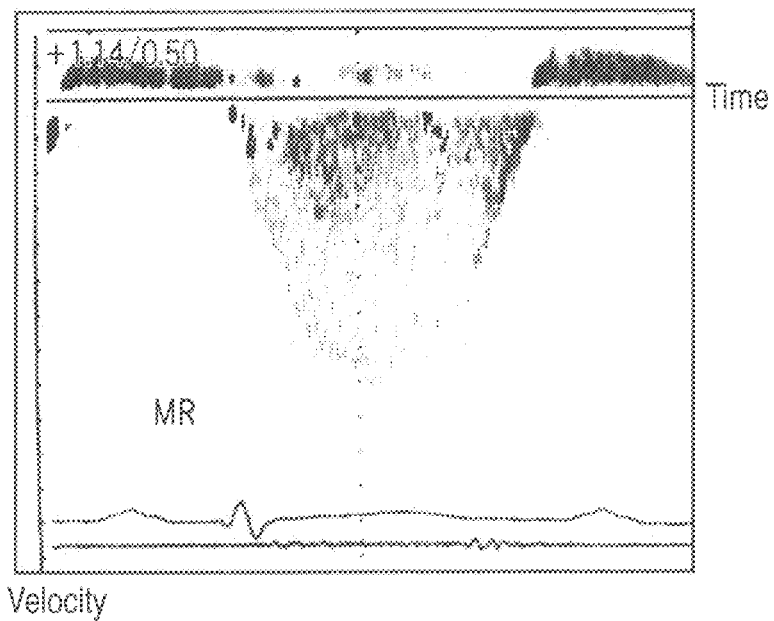
Figure 3A:
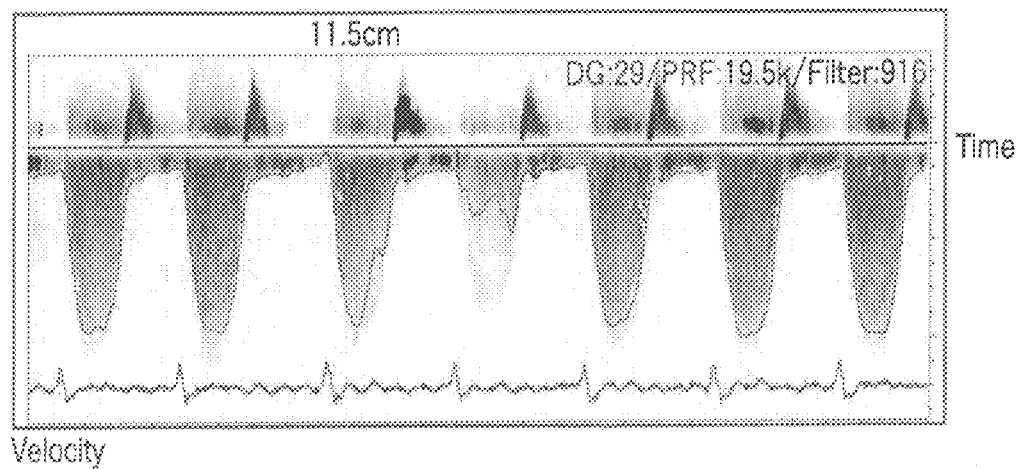
Figure 3B:
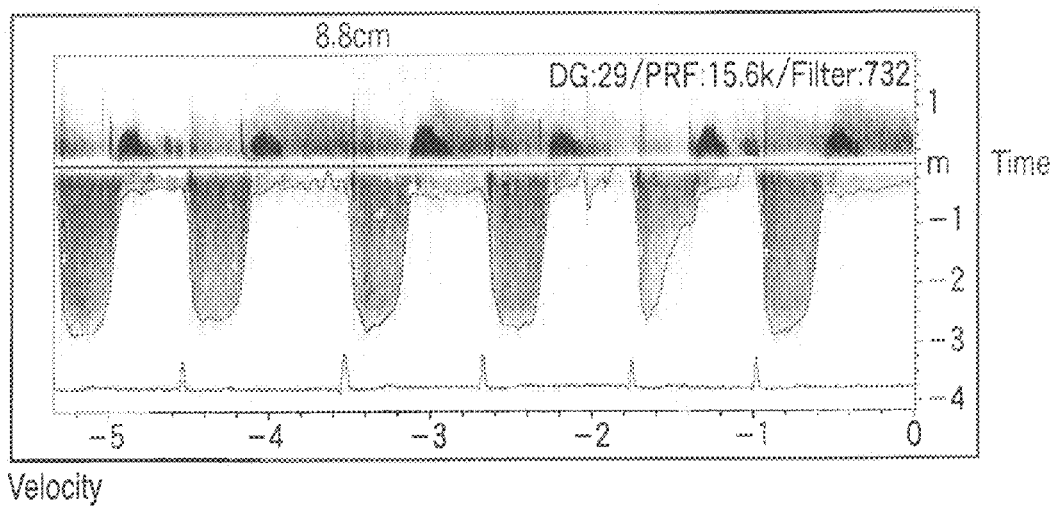

Doppler waveform correction of an ultrasonic diagnostic apparatus 1 will be described next. The Doppler spectra acquired by cardiac Doppler measurement may sometimes have losses and may not have sufficient intensity, as shown in FIGS. 2A and 2B. This is because the Doppler spectra are affected by unnecessary signals such as MR, TR, and PR originating from valve regurgitation and the like. Performing Doppler auto-trace processing for Doppler spectra with such losses and the like will generate trace waveforms with loss regions, as shown in FIGS. 3A and 3B. The timing of the occurrence of valve regurgitation, the direction and velocity of valve regurgitation, and the like vary depending on differences among patients (individual differences) and the types of valves. It is not therefore appropriate for the system to uniformly process such Doppler spectra.

When a loss portion exists in a trace waveform in this manner, this function makes the operator set at least one desired estimation point in consideration of individual differences and the types of valves, and interpolates the loss region by using the set estimation point, the periphery information of the trace waveform with the loss, and a predetermined function, thereby automatically correcting the trace waveform.

Note that this embodiment will exemplify a case in which this trace waveform correction function is to be implemented on an ultrasonic diagnostic apparatus. However, it is possible to implement this function by using a Doppler measurement apparatus or the like implemented by a medical workstation, a personal computer, or the like by installing a dedicated program. The Doppler measurement apparatus in this case includes, for example, the constituent elements inside the dotted line in FIG. 1.

Figure 4:
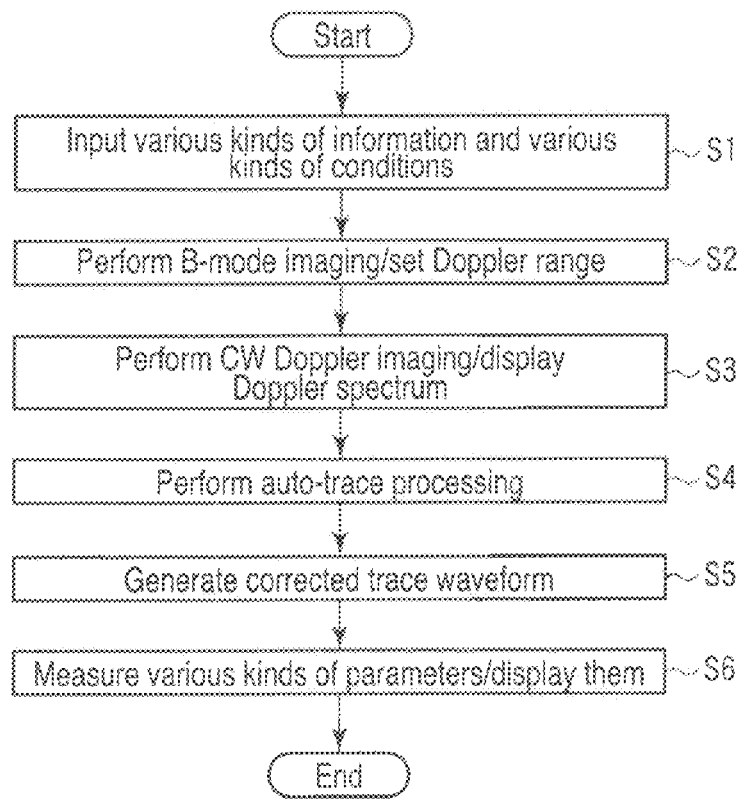
FIG. 4 is a flowchart showing a procedure for processing (trace waveform correction processing) based on a trace waveform correction function of this embodiment.

FIG. 4 is a flowchart showing a procedure for processing (trace waveform correction processing) based on this trace waveform correction function. The contents of each step executed in the trace waveform correction processing will be described with reference to FIG. 4.

First of all, the operator inputs patient information, imaging conditions used for B-mode imaging, and imaging conditions used for Doppler mode imaging (step S1). The control processor 28 then executes B-mode imaging in accordance with the input conditions, and displays a B-mode image on the monitor 14 in real time. In addition, the control processor 28 sets a range (Doppler measurement range) in which Doppler measurement is performed for the displayed B-mode image in response to an input from the input device 13 (step S2).

The control processor 28 then executes CW Doppler mode imaging in accordance with the input conditions and the set Doppler measurement range, and displays an ultrasonic image including time-series Doppler spectra on the monitor 14 in real time (step S3). The auto-trace processing unit 33 executes auto-trace processing by using the Doppler spectra acquired by CW Doppler mode imaging, and generates time-series trace waveforms (step S4).

If a loss exists in any one of the generated trace waveforms, the corrected trace waveform generation unit 35 then generates a corrected trace waveform by interpolating the loss region in accordance with the contents (to be described later) (step S5). The control processor 28 displays generated time-series trace waveforms (time-series trace waveforms including the corrected trace waveform obtained by interpolation processing if there is a loss region) on the monitor 14 in a predetermined form. In addition, the control processor 28 calculates various kinds of measurement values for the quantitative evaluation of the cardiac function based on the generated time-series trace waveforms and displays the values on the monitor 14 in a predetermined form (step S6).

(Generation Processing for Corrected Trace Waveform)

Generation processing for a corrected trace waveform in step S5 will be described in detail next.

Figure 5:
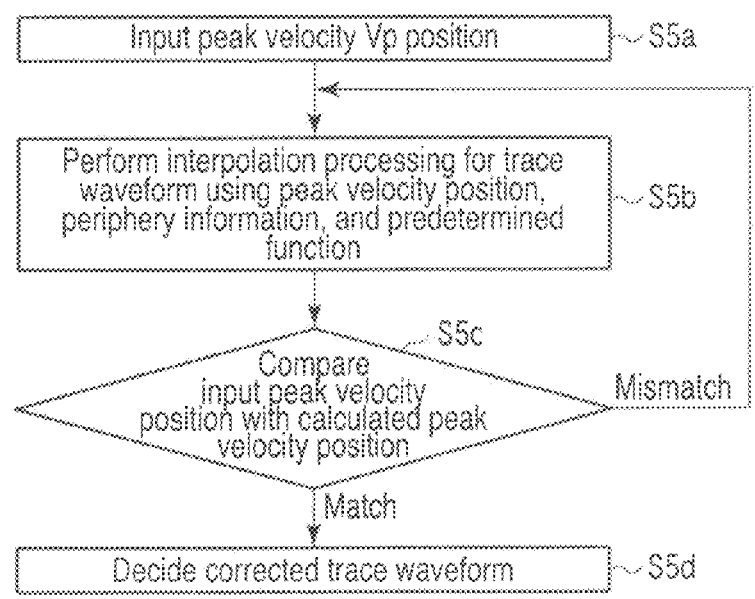
FIG. 5 is a flowchart showing a procedure for generation processing for a corrected trace waveform.

FIG. 5 is a flowchart showing a procedure for generation processing for a corrected trace waveform. The contents of each step for generation processing for a corrected trace waveform will be described with reference to FIG. 5.

[Step S5*a*: Input of Position of Peak Velocity Vp]

First of all, the operator inputs a position (point) corresponding to a peak velocity Vp via the input device 13 for a trace waveform in which a loss region exists (step S5*a*). The operator selects a trace waveform having a loss region (i.e., a trace waveform as a target for the generation of a corrected trace waveform) by using, for example, a predetermined device such as a trackball. In addition, the operator inputs a position (peak velocity position) corresponding to a peak velocity based on, for example, estimation by the operator by free-hand operation using a mouse or the like.

[Step S5*b*: Interpolation Processing Using Position of Peak Velocity Vp or Like]

Figure 6:
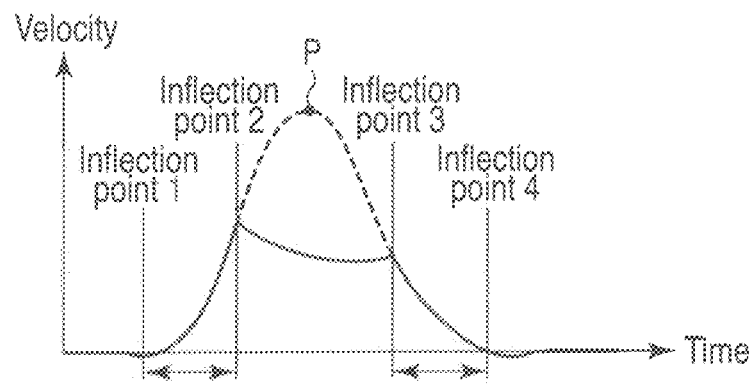
Figure 7:
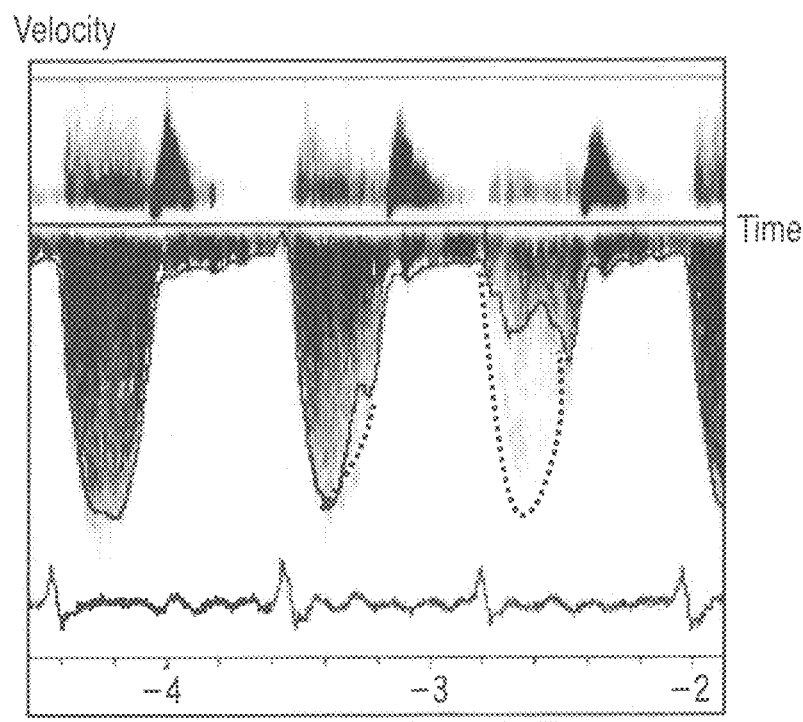

The corrected trace waveform generation unit 35 then executes the interpolation processing of interpolating the loss region of a trace waveform by using the input peak velocity position, the periphery information of the trace waveform having the loss region, and a predetermined function (step S5*b*). That is, as shown in FIG. 6, the corrected trace waveform generation unit 35 interpolates the loss region of the trace waveform by using an input peak velocity position P, inflection points 1, 2, 3, and 4 as periphery information of the trace waveform having the loss region, and, for example, a spline function. As a result of this interpolation processing, for example, a waveform like that indicated by the dotted line in FIG. 7.

[Steps S5*c*/S5*d*: Determination of Suitability of Peak Velocity Position/Decision of Corrected Trace Waveform]

The corrected trace waveform generation unit 35 then determines whether the peak velocity position of the interpolated trace waveform coincides with the peak velocity position input by free hand in step S5*a* (or falls within a predetermined allowable range) (step S5*c*). Upon determining as a result that the two peak velocity positions coincide with each other, the corrected trace waveform generation unit 35 decides the interpolated trace waveform as a corrected trace waveform. If the two peak velocity positions do not coincide with each other, the corrected trace waveform generation unit 35 interpolates the loss region of the trace waveform by using the input peak velocity position P, inflection points 1, 2, 3, and 4 of the periphery information of the trace waveform having the loss region, and a function (e.g., a cubic function) different from that used in step S5*b*, and decides the trace waveform obtained as a result of the interpolation as a corrected trace waveform (step 5*d*).

The above arrangement can obtain the following effects.

If a loss portion exists in a trace waveform in cardiac Doppler measurement, this ultrasonic diagnostic apparatus makes the operator set at least one desired estimation point in consideration of individual differences and the types of valves, interpolates the loss region by using the set estimation point, the periphery information of the trace waveform with the loss, and a predetermined function, and automatically generates a corrected trace waveform. Even if, therefore, a loss portion exists in a trace waveform, there is no need for the operator to manually correct each trace waveform or redo measurement. This can reduce the operation load in cardiac Doppler measurement and improve the diagnostic efficiency. In addition, in interpolating the loss portion of a trace waveform, for example, only a peak velocity position is artificially input by the operator, and the apparatus automatically calculates and generates a corrected trace waveform. It is therefore possible to reduce variations in measurement result among operators and implement Doppler measurement with high objectivity and reliability.

In addition, this ultrasonic diagnostic apparatus determines the suitability of an interpolated trace waveform based on the positional relationship between the peak velocity position of the interpolated trace waveform and the peak velocity position input by the operator. If this determination determines that the interpolated trace waveform is not suitable, the apparatus executes interpolation processing using a different function and generates a corrected trace waveform. Even if, therefore, the peak velocity position artificially set by the operator is not suitable, it is possible to generate a corrected trace waveform with high objectivity and reliability.

(Second Embodiment)

The second embodiment of the present application will be described. An ultrasonic diagnostic apparatus according to this embodiment automatically measures the feature amounts of left ventricular inflows and outflows corresponding to predetermined heartbeat periodicities (for example, heartbeat periodicities corresponding to all the Doppler spectra or all the trace waveforms displayed on the screen), and automatically calculates mean measurement values associated with the predetermined cardiac rates. The apparatus then displays the calculated values in a predetermined form.

Figure 8:
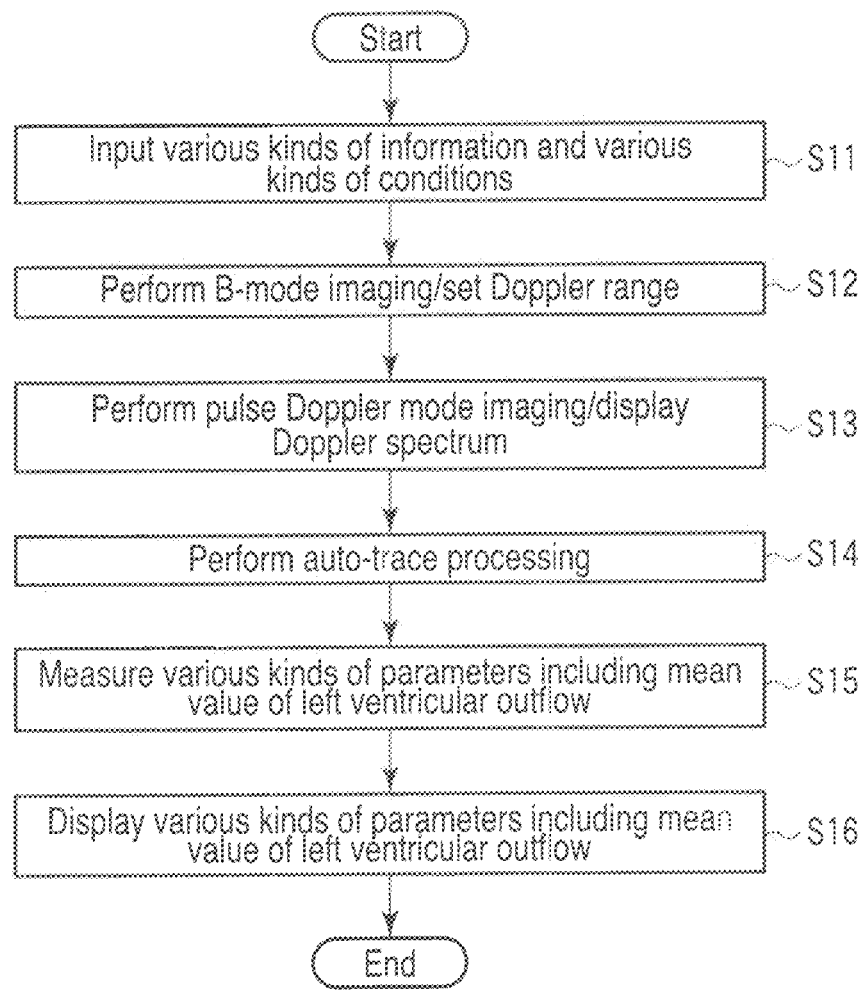
FIG. 8 is a flowchart showing a procedure for Doppler measurement processing according to the second embodiment.

FIG. 8 is a flowchart showing a procedure for Doppler measurement processing according to the second embodiment. The contents of each step executed in Doppler measurement processing will be described with reference to FIG. 8.

Figure 9:
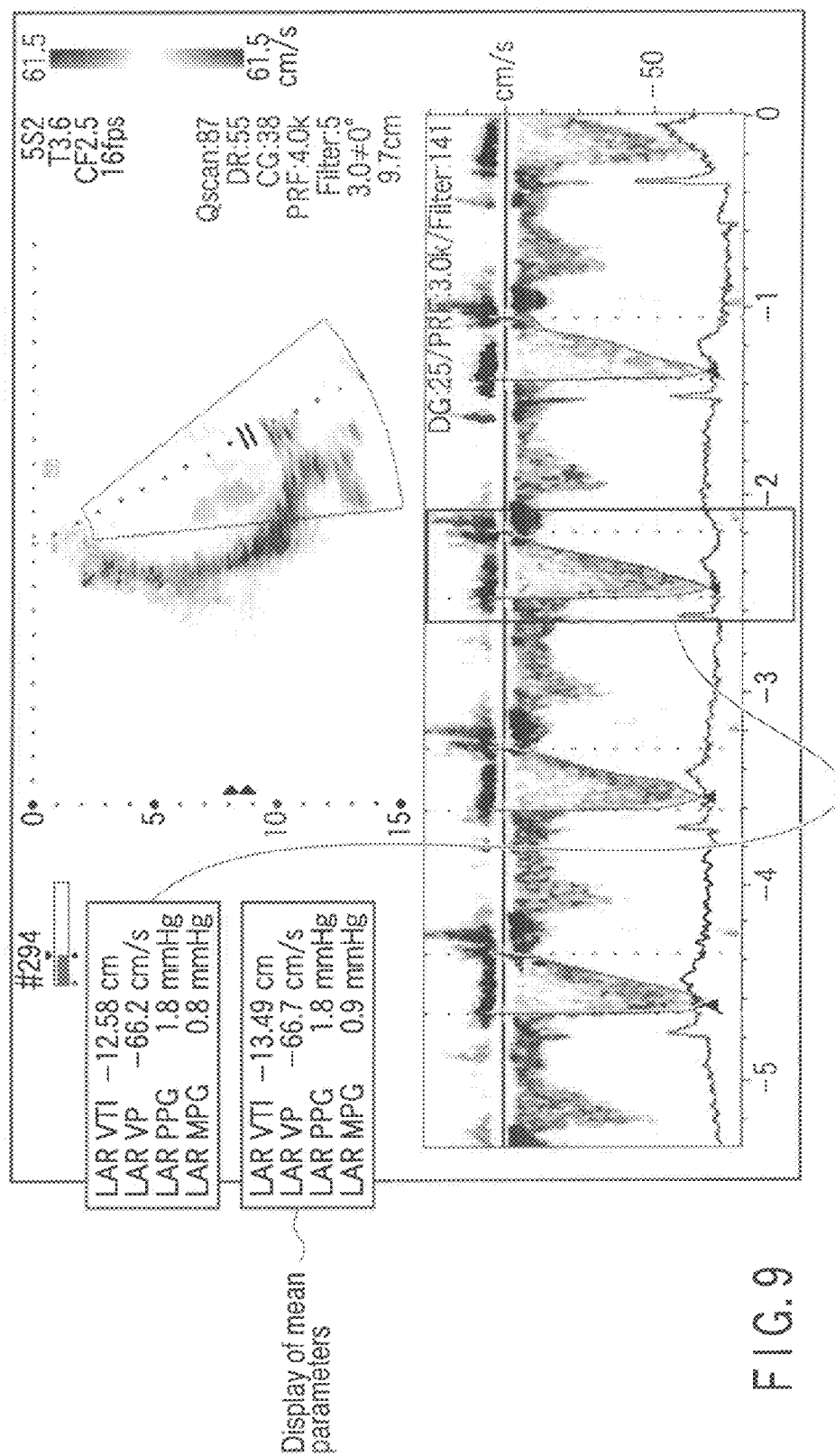
FIG. 9 is a view showing an example of the display form of various kinds of feature amounts associated with a left ventricular outflow according to the second embodiment.

First of all, the operator inputs patient information, imaging conditions used for B-mode imaging, and imaging conditions used for Doppler mode imaging (step S11). A control processor 28 then executes B-mode imaging in accordance with the input conditions and displays the B-mode image on a monitor 14 in real time. The control processor 28 sets a range (Doppler measurement range) in which Doppler measurement is performed for the displayed B-mode image in response to an input from an input device 13 (step S12). Assume that in this embodiment, a Doppler measurement range is set in a predetermined region (see, for example, FIG. 9) for the measurement of a left ventricle outflow.

The control processor 28 then executes pulse Doppler imaging in accordance with the input conditions and the set Doppler measurement range, and displays an ultrasonic image including time-series Doppler spectra on the monitor 14 in real time (step S13). An auto-trace processing unit 33 executes auto-trace processing by using the Doppler spectra acquired by CW Doppler mode imaging, and generates time-series trace waveforms (step S14).

The control processor 28 then calculates, for each left ventricular outflow, VTI (blood flow velocity–time integration) at a predetermined heartbeat selected by the operator using a trackball, VP (peak systolic velocity), PPG (Peak Pressure Gradient), and MPG (Mean Pressure Gradient). The control processor 28 also calculates a mean VTI, mean VP, mean PPG, and mean MPG associated with a predetermined heartbeat periodicity by using a plurality of displayed time-series trace waveforms (step S15). The control processor 28 displays a feature amount associated with the calculated blood flow on the monitor 14 in the form shown in FIG. 9 (step S16).

Figure 10:
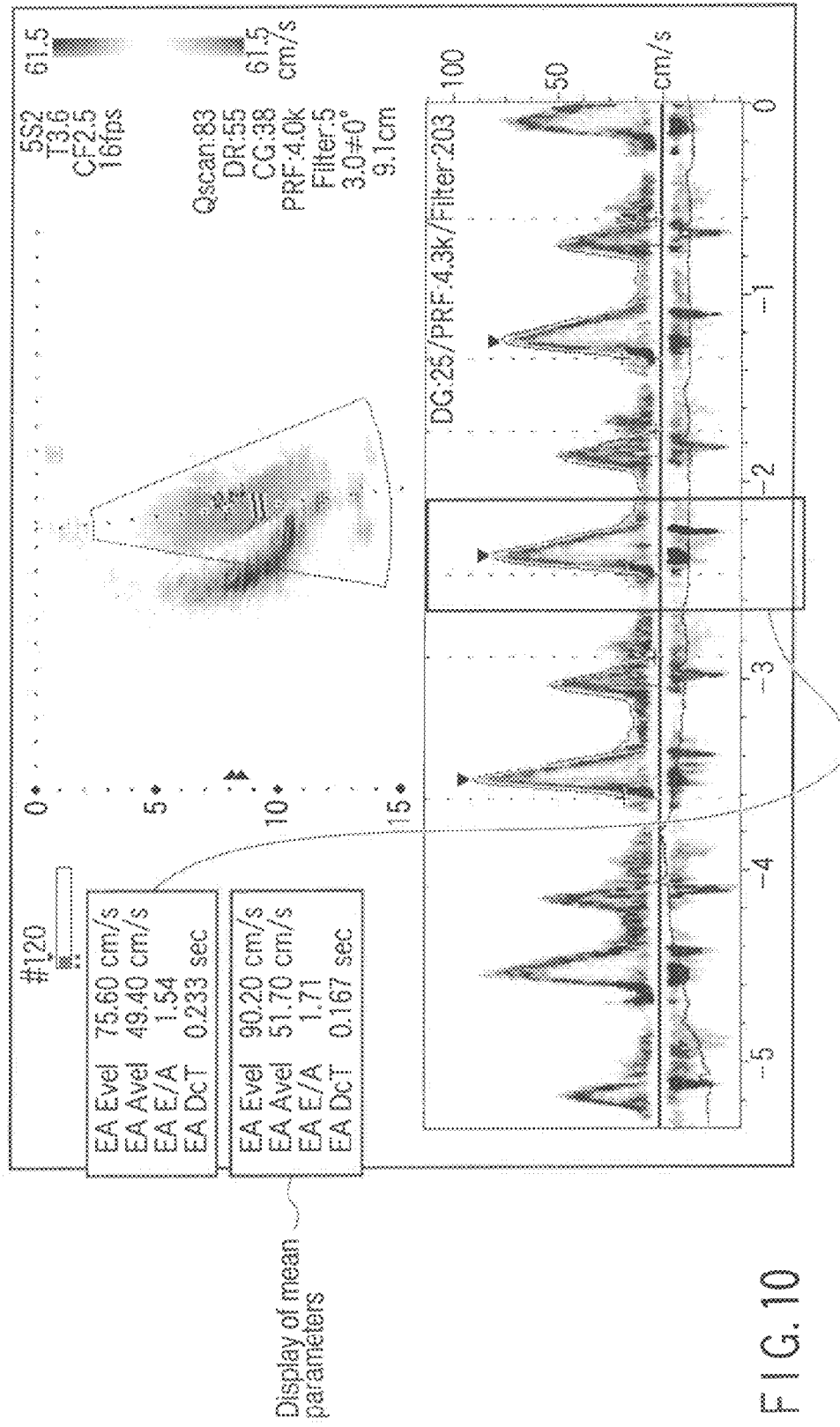
FIG. 10 is a view showing an example of the display form of various kinds of feature amounts associated with a left ventricular inflow according to the second embodiment.

The same substantially applies to the measurement of a left ventricular inflow. FIG. 10 shows an example of the display form of various kinds of feature amounts associated with a left ventricular inflow.

The above arrangement can obtain the following effects.

Figure 11:
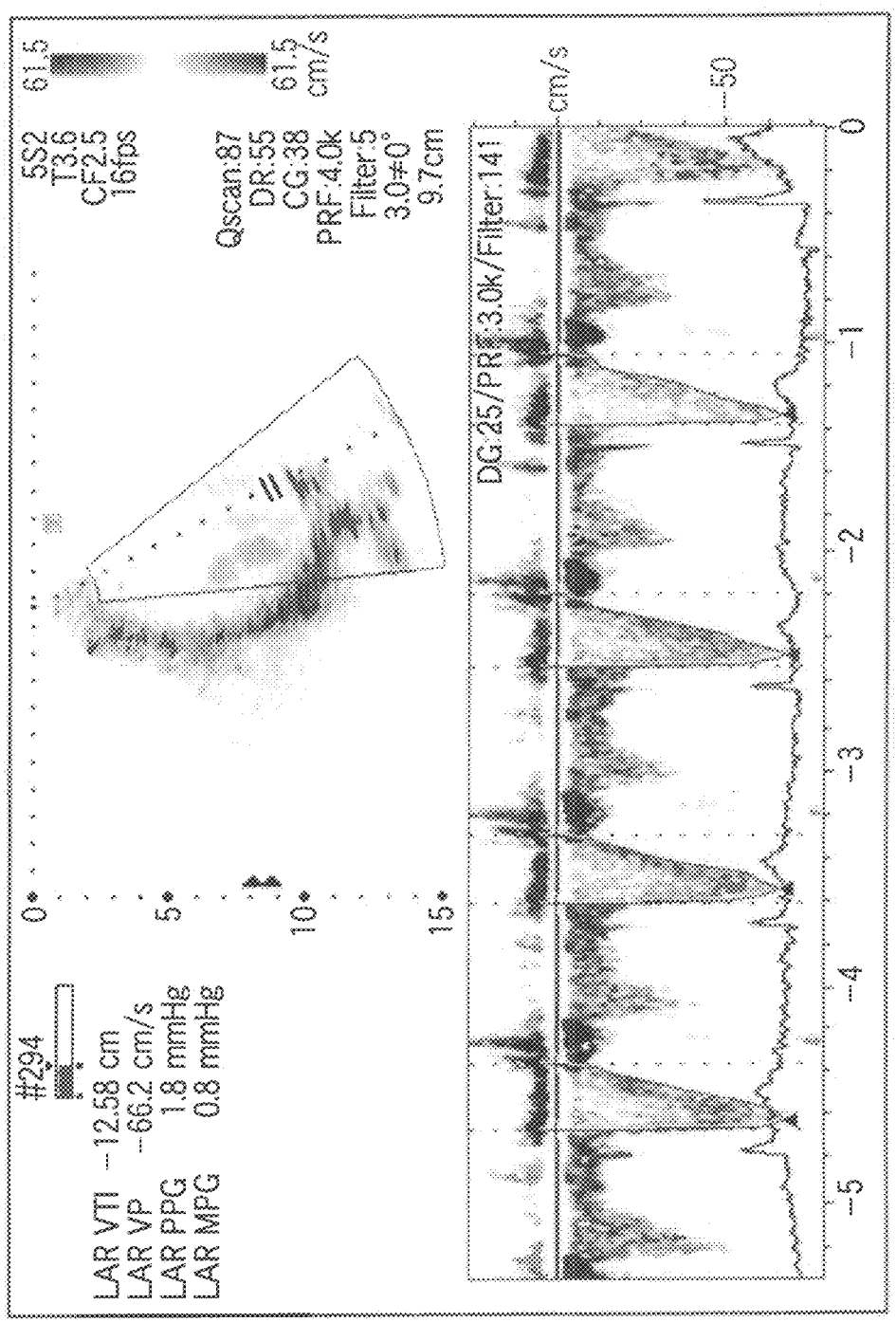
FIG. 11 is a view showing an example of the display form of various kinds of feature amounts associated with a left ventricular outflow according to the prior art.

Conventionally, various kinds of measurement values corresponding to each heartbeat displayed as shown in FIG. 11 are recorded individually, and mean measurement values associated with a plurality of heart rates are acquired separately by artificial calculation. In contrast, this ultrasonic diagnostic apparatus automatically measures, in cardiac Doppler measurement, the feature amounts of left ventricular outflows and the like corresponding to heartbeat periodicities corresponding to all the Doppler spectra or all the trace waveforms displayed on the screen, and automatically calculates mean measurement values associated with the cardiac rates. The apparatus then displays the calculated values in a predetermined form. It is therefore unnecessary to manually calculate a measurement value or feature amount from a selected Doppler spectrum or trace waveform. This can reduce the operation load in cardiac Doppler measurement and improve the diagnostic efficiency.

(Third Embodiment)

The third embodiment of the present application will be described. When acquiring a plurality of Doppler spectra (or trace waveforms) corresponding to different places or different heartbeats of the heart in the Doppler mode, an ultrasonic diagnostic apparatus according to this embodiment simultaneously displays Doppler spectra in correspondence with cardiac phases, thereby automatically performing measurement. For a concrete description, the following will exemplify a case in which the apparatus performs Doppler measurement in different heartbeats with respect to two positions, i.e., the left ventricular inflow position and the left ventricular outflow position. However, the present application is not limited to this example. The technical idea of the present application can be applied to even a case in which Doppler measurement is performed in different heartbeats at three or more different places.

Figure 12:
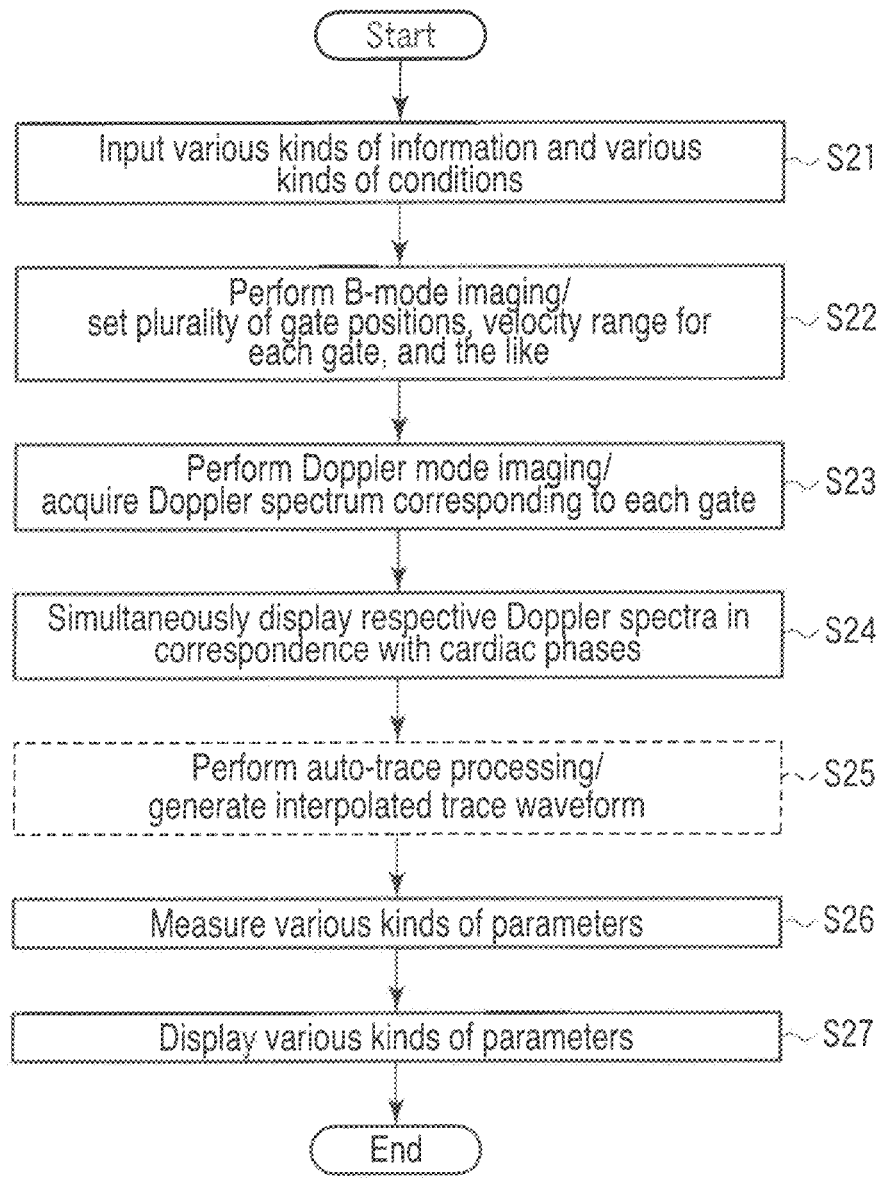
FIG. 12 is a flowchart showing a procedure for Doppler measurement processing according to the third embodiment.

FIG. 12 is a flowchart showing a procedure for Doppler measurement processing according to the third embodiment. The contents of each step executed in Doppler measurement processing will be described with reference to FIG. 12.

First of all, the operator inputs patient information, imaging conditions used for B-mode imaging, and imaging conditions for Doppler mode imaging (step S21).

A control processor 28 then executes B-mode imaging in accordance with the input conditions and displays a B-mode image on a monitor 14 in real time. The control processor 28 sets a Doppler measurement gate (to be also simply referred to as a "gate") at a position at which Doppler measurement is performed for the displayed B-mode image, in accordance with an input from an input device 13 (step S22). Assume that in this embodiment, Doppler measurement gates are set at two positions, i.e., a left ventricular inflow position (first gate G1) and a left ventricular outflow position (second gate G2), as shown in FIG. 13. The control processor 28 sets a velocity range and gain in Doppler measurement for each gate in response to an input from the input device 13. For each of a plurality of Doppler gates set at different positions, an independent ultrasonic propagation path, velocity range, and gain are set, and independent Doppler measurement is executed. It is therefore possible to regard Doppler measurement for each gate position as independent Doppler measurement at each of different channels.

The control processor 28 then executes pulse Doppler mode imaging for each gate position in synchronism with ECG in accordance with the input conditions, and acquires a Doppler spectrum corresponding to each gate position (step S23). For example, the control processor 28 executes Doppler mode imaging at a first gate G1 shown in FIG. 13 as a measurement position at first for a predetermined period corresponding to at least one or more heartbeats in synchronism with ECG, and acquires a Doppler spectrum corresponding to the first gate G1 in the predetermined period. After the end of Doppler mode imaging corresponding to the first gate G1, the control processor 28 executes Doppler mode imaging at a second gate G2 shown in FIG. 15 as a measurement position at first for a predetermined period corresponding to at least one or more heartbeats in synchronism with ECG, and acquires a Doppler spectrum corresponding to the second gate G2 in the predetermined period. Note that it is possible to alternately and repeatedly execute Doppler mode imaging corresponding to the first gate G1 and Doppler mode imaging corresponding to the second gate G2, as needed.

As shown in FIG. 13, the control processor 28 then simultaneously displays a first Doppler spectrum LVI corresponding to the first gate G1 as a measurement position (i.e., associated with the left ventricular inflow position) and a second Doppler spectrum LVO corresponding to the second gate G2 as a measurement position (i.e., associated with the left ventricular outflow) in correspondence with cardiac phases (step S24). At this time, the monitor 14 displays each spectrum with a margin including at least a predetermined period before and after the time of the generation of an R wave of an ECG waveform (for example, a period of 300 ms before and after the time of the generation) in correspondence with each ECG waveform.

The apparatus then performs auto-trace processing, generation of an interpolated trace waveform according to the first embodiment, or the like, as needed (step S25).

The operator then designates various kinds of periods for the calculation of IRT and ICT as measurement parameters with the trackball or the like for the first and second Doppler spectra simultaneously displayed in correspondence with the cardiac phases. The control processor 28 calculates IRT and ICT as measurement parameters by using the designated various kinds of periods (step S26).

Figure 14:
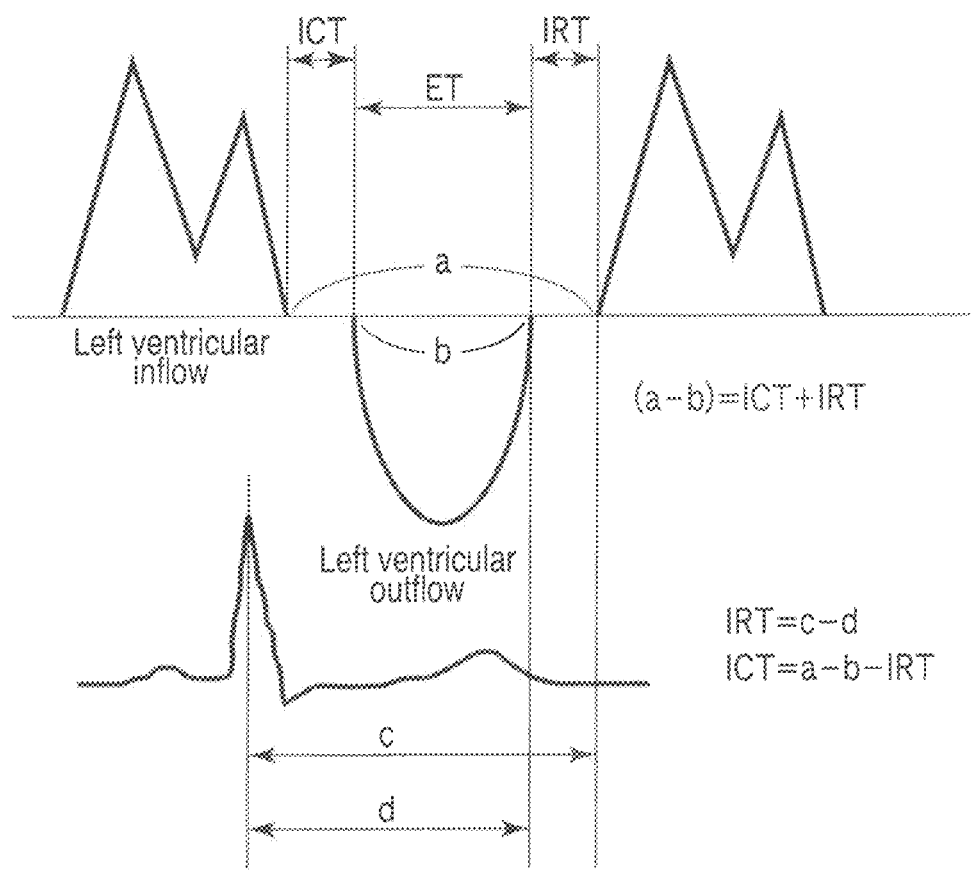
FIG. 14 is a view for explaining the relationship between each kind of period designated in step S25 described above and IRT and ICT.

FIG. 14 is a view for explaining the relationship between various kinds of periods designated in step S26 described above, IRT, and ICT. FIG. 14 simultaneously shows, in a simplified form, part of the first Doppler spectrum LVI and part of the second Doppler spectrum LVO associated with a heartbeat i in correspondence with the cardiac phases. Letting h(i) be one heartbeat period, and a'(i) be the diastolic period based on an E wave and an A wave, a(i)=h(i)–a'(i). Letting b(i), c(i), and d(i) be the periods shown in FIG. 14, the following relational expressions hold between a(i), b(i), c(i), d(i), IRT, and ICT:

$$(a-b)=iCT+iRT \quad (1)$$

$$iRT=c(i)-d(i) \quad (2)$$

$$ICT=a(i)-b(i)-IRT \quad (3)$$

The operator can therefore easily and quickly comprehend and designate the periods a(i) and b(i) manually while comparing/referring to the first and second Doppler spectra LVI and LVO simultaneously displayed in correspondence with the cardiac phases, as shown in FIG. 13. The monitor 14 displays each spectrum, in particular, with a margin including at least a predetermined period before and after the time of the generation of an R wave of an ECG waveform (for example, a period of 300 ms before and after the time of the generation) in correspondence with each ECG waveform. It is therefore possible to accurately designate the periods a(i) and b(i) while comprehending the correspondence between the first Doppler spectrum LVI and the second Doppler spectrum LVO.

The control processor 28 displays the calculated values of measurement parameters in a predetermined form on the monitor 14 (step S27).

(Modification)

The above description has exemplified the case in which the apparatus performs Doppler measurement in different heartbeats at two positions, i.e., the left ventricular inflow position and the left ventricular outflow position. The technical idea of the present application is not limited to this example, and is very effective for a case in which, for example, the apparatus measures a measurement value (E/e') calculated by using a right ventricular inflow and a mitral annulus velocity.

FIG. 15 is a view showing an example of a first Doppler spectrum E and a second Doppler spectrum e' which are displayed in correspondence with cardiac phases when the apparatus executes blood flow Doppler measurement upon setting the first gate G1 at the right ventricular inflow position and executes tissue Doppler measurement upon setting the second gate G2 at the mitral annulus ring. As shown in FIG. 15, the operator can easily and quickly comprehend and designate the maximum and minimum values in each corresponding heartbeat while comparing and referring to the first Doppler spectrum E and the second spectrum e' simultaneously displayed in correspondence with the cardiac phases.

The above arrangement can obtain the following effects.

Upon acquiring a plurality of Doppler spectra corresponding to different places or different heartbeats of the heart by the Doppler mode, this ultrasonic diagnostic apparatus simultaneously displays these spectra in correspondence with cardiac phases. When, therefore, executing parameter measurement using a plurality of Doppler spectra corresponding to different places or different heartbeats of the heart, it is possible to visually and intuitively comprehend periods and values to be designated. This can reduce the operation load on the operator and improve the operation efficiency in image diagnosis.

In addition, this ultrasonic diagnostic apparatus executes Doppler measurement independently for a plurality of gates set at different places of the heart by using independent ultrasonic propagation paths, velocity ranges, and gains. It is therefore possible to freely set suitable velocity ranges and gains in accordance with individual differences among objects to be examined and the respective measurement positions. This makes it possible to implement accurate Doppler measurement without any aliasing and contribute to an improvement in the quality of image diagnosis.

Note that the present application is not limited to the above embodiments, and constituent elements can be variously modified and embodied at the execution stage within the spirit and scope of the application. The following are concrete modifications.

(1) Each function associated with each embodiment can also be implemented by installing programs for executing the corresponding processing in a computer such as a workstation and expanding them in a memory. In this case, the programs which can cause the computer to execute the corresponding techniques can be distributed by being stored in recording media such as magnetic disks ((Floppy®) disks, hard disks, and the like), optical disks (CD-ROMs, DVDs, and the like), and semiconductor memories.

(2) The first embodiment described above is configured to cause the corrected trace waveform generation unit 35 to execute corrected trace waveform generation processing when the operator specifies a trace waveform with a loss region and inputs a point corresponding to a peak velocity position relative to the specified trace waveform. In contrast, the corrected trace waveform generation unit 35 may automatically determine a trace waveform with a loss region and prompt the operator to input a peak velocity position with respect to the trace waveform with the loss region.

(3) The first embodiment described above is configured to input only a peak velocity position (point) with respect to a trace waveform with a loss region by using a predetermined device. However, it is possible to input a plurality of estimation points including a peak velocity position with respect to a trace waveform with a loss region and interpolate the loss region using them without being limited to the above arrangement.

In addition, various inventions can be formed by proper combinations of a plurality of constituent elements disclosed in the above embodiments. For example, several constituent elements may be omitted from all the constituent elements disclosed in the above embodiments. Furthermore, constituent elements in different embodiments may be properly combined.

It is possible to implement an ultrasonic diagnostic apparatus, Doppler measurement apparatus, and Doppler measurement method which can automate or semi-automate various kinds of manual procedures occupying most of the operation in cardiac Doppler measurement, and attribute to a reduction in operation load in cardiac Doppler measurement, an improvement in operation efficiency, and a reduction in variations in measurement result.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
   a Doppler processing circuit configured to generate a Doppler spectrum from an ultrasonic signal reflected from a predetermined region in a heart;
   a control processing circuit configured to generate temporal changes in a predetermined spectrum component in the Doppler spectrum as a plurality of trace waveforms, and generate a corrected trace waveform by interpolating a trace waveform of the plurality of trace waveforms that has a loss portion, using an estimation point input for the trace waveform, the estimation point specifying a blood flow velocity at a given time, wherein the control processing circuit is configured to generate the corrected trace waveform so that the corrected trace waveform passes through the estimation point; and
   a display configured to output a plurality of trace waveforms including the corrected trace waveform.

2. The ultrasonic diagnostic apparatus according to claim 1, wherein the control processing circuit is further configured to determine whether a waveform loss due to valve regurgitation exists in any of the plurality of trace waveforms, wherein
   the display is configured to output the trace waveform determined as having the loss in a form different from that of other trace waveforms.

3. The ultrasonic diagnostic apparatus according to claim 1, wherein the control processing circuit is further configured to decide an interpolation function used for the interpolation based on the at least one input estimation point, and generate the corrected trace waveform by using the decided interpolation function.

4. The ultrasonic diagnostic apparatus according to claim 1, wherein the control processing circuit is further configured to generate a first trace waveform by using the at least one input estimation point, the trace waveform having the loss portion, and a predetermined interpolation function,
   determine whether the first trace waveform is suitable as the corrected trace waveform, by comparing the first trace waveform with the at least one input estimation point,
   decide the first trace waveform as the corrected trace waveform when the determination determines that the first trace waveform is suitable, and
   generate a second trace waveform by using the at least one input estimation point, the trace waveform having the loss portion, and another interpolation function different from the predetermined interpolation function, when the determination determines that the first trace waveform is not suitable, and decide the second trace waveform as the corrected trace waveform.

5. The ultrasonic diagnostic apparatus according to claim 1, further comprising input hardware which inputs the estimation point.

6. The ultrasonic diagnostic apparatus according to claim 1, wherein when the estimation point is input, the display is further configured to display the plurality of trace waveforms including the estimation point at least one of before and after generation of the corrected trace waveform.

7. The ultrasonic diagnostic apparatus of claim 1, wherein the control processing unit is further configured to determine whether or not a blood flow velocity value of the corrected trace waveform matches a blood flow velocity value of the estimation point at the given time, and regenerate a corrected trace waveform if the blood flow velocity values do not match.

8. The ultrasonic diagnostic apparatus of claim 1, wherein the control processing circuit is configured to generate the corrected trace waveform using a plurality of estimation points, including a peak velocity position.

9. A Doppler measurement apparatus, comprising:
   a Doppler processing circuit configured to generate a Doppler spectrum from an ultrasonic signal reflected from a predetermined region in a heart;
   a control processing circuit configured to generate temporal changes in a predetermined spectrum component in the Doppler spectrum as a plurality of trace waveforms, and generate a corrected trace waveform by interpolating a trace waveform of the plurality of trace waveforms that has a loss portion, using an estimation point input for the trace waveform, the estimation point specifying a blood flow velocity at a given time, wherein the corrected trace waveform generation unit is configured to generate the corrected trace waveform so that the corrected trace waveform passes through the estimation point; and a display configured to output a plurality of trace waveforms including the corrected trace waveform.

10. A Doppler measurement method using an ultrasonic diagnostic apparatus, comprising:

generating a Doppler spectrum from an ultrasonic signal reflected from a predetermined region in a heart;

generating temporal changes in a predetermined spectrum component in the Doppler spectrum as a plurality of trace waveforms;

generating a corrected trace waveform by interpolating a trace waveform of the plurality of trace waveforms that has a loss portion, using an estimation point input for the trace waveform, the estimation point specifying a blood flow velocity at a given time, wherein the generating step generates the corrected trace waveform so that the corrected trace waveform passes through the estimation point; and outputting a plurality of trace waveforms including the corrected trace waveform.

* * * * *